United States Patent [19]

Evers

[11] 4,167,562

[45] Sep. 11, 1979

[54] METHOD AND COMPOSITION FOR TREATING ARTERIOSCLEROSIS

[76] Inventor: H. Ray Evers, P. O. Box 2805, Montgomery, Ala. 36105

[21] Appl. No.: 937,533

[22] Filed: Aug. 28, 1978

[51] Int. Cl.² ............... A61K 33/14; A61K 37/40; A61K 31/725; A61K 31/68

[52] U.S. Cl. .................... 424/153; 424/179; 424/183; 424/201; 424/252; 424/255; 424/263; 424/270; 424/280; 424/317; 424/319

[58] Field of Search ........... 424/153, 183, 179, 252, 424/263, 201, 255, 270, 280, 317, 319

[56] References Cited

U.S. PATENT DOCUMENTS

| | | | |
|---|---|---|---|
| 3,089,815 | 5/1963 | Liev et al. | 424/183 |
| 3,574,831 | 4/1971 | Engel et al. | 424/183 |
| 3,887,705 | 6/1975 | Serre et al. | 424/261 |
| 3,932,656 | 1/1976 | Ramwell et al. | 424/16 |
| 4,039,665 | 8/1977 | Foley | 424/183 |

OTHER PUBLICATIONS

The Pharmacological Basis of Therapeutics, pp. 1459–1462, 1624–1625, 1634–1636, 1643, 1654, 1655 and 1662–1664, (1966).

The Merck Index, 9th ed. (1976) cites 157, 1666, 1701, 4510, 4687, 5485, 5518, 7766, 8323, 9024 and 9670.

The Pharmacopeia of the U.S.A., 18th Rev. (1970) pp. 593–594.

*Primary Examiner*—Douglas W. Robinson
*Attorney, Agent, or Firm*—Duckworth, Hobby, Allen & Pettis

[57] ABSTRACT

New compositions and their method of use for treating cardiovascular diseases primarily due to arteriosclerosis and atherosclerosis. These new compositions are prepared from a base Ringers injection to which is added a B-complex, hydrochloric acid, sodium ascorbate, pyridoxine hydrochloride, magnesium sulfate, adrenal cortex, magnesium chloride, thiamine, heparin sodium, calcium gluconate and calcium d-saccharate. Additional embodiments of the solution composition are also disclosed containing niacin, vitamin $B_{12}$, ether, algae and amino acids. The compositions are useful in removing plaques from the interior walls of the arteries and veins, thereby improving blood supply to body tissues.

11 Claims, No Drawings

METHOD AND COMPOSITION FOR TREATING ARTERIOSCLEROSIS

BACKGROUND OF THE INVENTION

1. Field of the Invention

The present invention relates to new compositions in the nature of intravenous solutions useful for treating cardiovascular diseases, as well as the method of intravenously infusing the composition solution into the blood of the patient.

2. Description of the Prior Art

It is a well known fact that, in the United States, heart disease and associated maladies and disfunctions are a primary cause of death. Two types of diseases significantly contributing to the high mortality rate attributed to heart disease are arteriosclerosis and atherosclerosis. The first of these diseases is characterized by abnormal thickening and hardening of the arterial walls, while the second is characterized by the deposition of fatty substances in and fibrosis of the inner layer of the arteries. Numerous attempts have been made at successfully treating both these diseases such as, for example, medication, diet control and regulation, exercise, and even surgery. Within the area of treatment by medication, the medicament often administered does not actually treat the condition, but attempts to maintain the blood in a fluid state by inhibiting coagulation. Heparin is oftentimes administered for this purpose. U.S. Pat. No. 3,574,831, discloses a composition suitable for this purpose. A related disclosure concerning an article of manufacture for instant release of anti-aggregation and non-thrombogenic agents to biological media is shown in U.S. Pat. No. 3,932,656. Other methods and compositions for the treatment of venous deficiencies and blemishes are taught in U.S. Pat. Nos. 3,887,705 and 4,039,665. However, it should be noted that U.S. Pat. No. 4,039,665 actually calls for treatment with heparin as a sclerosing agent. Clearly then, while the use of heparin is recognized as an anticoagulant, its use for actually treating a sclerotic condition is contraindicated.

Accordingly, it is clear that there is a great need in the art for an effective treatment medication and method not only for enabling the body to deal with the deleterious effects of sclerosis, but more importantly for actually treating and reducing the sclerotic condition. Of course, such a composition must be suitable for administering to humans, and it would be further desirable if the composition could be administered using relatively simple and safe techniques.

SUMMARY OF THE INVENTION

The present invention relates to a solution composition and its method of use for treating cardiovascular diseases primarily due to arteriosclerosis and atherosclerosis. During the past two decades the entire medical profession has witnessed the birth of what may best be termed a wholistic approach to medicine which has resulted in an emphasis not just on treating a physiological illness or malfunction, but also on correct diagnosis, chemical balance within the body, proper nutrition and physical medicine. It is as a direct result of such a wholistic approach that the present method and composition for treating cardiovascular diseases has been developed.

Most simply stated, this invention relates to a method of intravenous infusion of a solution composition which has been demonstrated as being efficacious in actually removing the plaques found on the inner walls of sclerotic veins and arteries.

While the solution composition and method will be described in greater detail below, it should also be noted that the administration of adjunctive therapies has also been found to improve the patient's condition. These therapies consist of the administration of citric acid orally, as well as the administration of many natural minerals and vitamins to improve the general nutrition of the body in order to rebuild and bring the body chemistry into proper balance. As stated above, this invention actually removes the plaques and improves the blood supply to all the tissues and organs of the body. The beneficial results are attributed to the increased blood supply in combination with better nutrients in the blood stream and more oxygen being provided to the body's tissues.

A standard Ringers solution is utilized as the base material for the intravenously injected composition. Ringers injection is a standard saline solution consisting of sodium chloride, potassium chloride and calcium chloride. Analytical analysis of the standard Ringers solution reveals the following, expressed in milligrams (mg) per ten milliliters (ml) of Ringers solution:

Sodium chloride: 86 mg
Potassium chloride: 3 mg
Calcium chloride: 3.3 mg

The intravenous solution of the present invention is then prepared by adding the following ingredients. All ingredients are expressed in terms of quantity per ten ml of Ringers solution.

B-complex: 1,000–5,000 mg
Hydrochloric acid U.S.P.: 10–40 mg
Sodium ascorbate: 500–25,000 mg
Pyridoxine hydrochloride: 500–5,000 mg
Magnesium sulfate: 100–2,500 mg
Adrenal cortex: 250–2,500 mcg
Magnesium chloride: 250–5,000 mg
Thiamine: 100–2,000 mg
Heparin sodium: 2,500–25,000 U.S.P. units
Calcium gluconate: 250–2,500 mg
Calcium d-saccharate: 1.6–5.0 mg With regard to the above composition it should be noted that the constituents for the B-complex are methioine, cholinechloride, thiamine hydrochloride, niacinamide, riboflavin, pyridoxine hydrochloride, d'pantothenyl alcohol and inactive benzyl alcohol N.F. 1.5% in water.

The above composition, then, sets forth the basic intravenous solution of the present invention. More precise examples of its formulation will be presented hereinafter.

At this point it should also be noted that actual clinical useage and observation have revealed the desirability of what may best be described as "fortification" of the basic intravenous solution dependent upon the individual patient's condition. Such "fortification" is accomplished by addition of one or more of the following ingredients to the basic solution of this invention. In the listing presented below quantities are expressed per 500 ml of the intravenous solution.

Niacin: 100–1,000 mg
$B_{12}$: 100–1,000 mcg
Ether: 2–10 cc
Algae: 250–1,000 mg
Amino acids: 2–10 g As above, the "fortified" solution is then administered intravenously, whereby sclerotic plaques are actually removed, thereby enhancing the patients physiological condition.

The invention accordingly comprises the several steps in the relation of one or more of such steps with respect to each of the others, and the composition possessing the features, properties, and the relation of components which are exemplified in the following detailed description, and the scope of the invention will be indicated in the claims.

DETAILED DESCRIPTION

The present invention relates to an intravenous solution useful in the treatment of cardiovascular diseases primarily due to arteriosclerosis and atherosclerosis. In order to determine the efficacy of the various formulations of the composition differing formulations were administered to patients and their effectiveness for the primary purpose of removing plaques was determined by subsequent examination.

The following examples, then, are set forth in order to fully describe the composition and its method of use both with regard to the present invention.

This method of chemo endarterectomy therapy is one in which a prepared solution is given intravenously, by the use of a butter fly needle, in the vein of the patient to whom it is indicated needs this type of therapy. The way the chemical solution works in that the chelating substances have a negative valence of two. When this substance enters the blood stream the molecules of the chelating agents, having this negative valence of two, attract the positive charged metals with a positive valence of two, so that it is by bonding reaction that the chelating agents pull the metals out of the walls of the arteries. Once the metals are removed, then the cholesterol and triglycerides dissolve in the blood stream and are excreted by way of the urinary track. One can monitor the urinary output on a 24 hour basis and recover this material, and one can monitor the patient at the beginning of the treatment and during the course of treatment to measure the amount that is removed by this process. The way this works is that the chelating agents remove the inorganic calcium from the blood stream thereby lowering the calcium to the extent that the parathyroid gland is stimulated and excretes parathyroid hormone which removes the calcium from the various areas of the body to rebuild the calcium in the blood steam to its normal level. The chemical process works in this manner, and its efficacy has been proven both bio-chemically and physiologically.

EXAMPLE I

The qualitative and quantitative data presented below set forth in a preferred embodiment for the intravenous solution of the present invention. When prepared in accord with the below formulation, the solution was administered by intravenous infusion.

As a starting, or base, material 500 ml of standard Ringers injection was selected. Qualitative and quantitative analysis of the standard Ringers injection revealed the following, expressed as quantity per 10 ml of injection:

Sodium chloride: 86.0 mg
Potassium chloride: 3.0 mg
Calcium chloride: 3.3 mg

The intravenous solution of the present invenion was prepared by adding thereto the following constituents, expressed as quantity per 10 ml:

| | | |
|---|---|---:|
| A. | B-complex | |
| | a. Methioine N.V. | 125 mg |
| | b. Cholinechloride U.S.P. | 500 mg |
| | c. Thiamine hydrochloride U.S.P. | 500 mg |
| | d. Niacinamide U.S.P. | 1,000 mg |
| | e. Riboflavin-5'-phosphate sodium | 20 mg |
| | f. Pyridoxine hydrochloride U.S.P. | 20 mg |
| | g. d'Pantothenyl alcohol | 20 mg |
| | h. Inactive-benzyl alcohol N.F. 1.5% in water | |
| | Total B-complex | 2,185 mg |
| B. | Hydrochloric acid U.S.P. | 20 mg |
| C. | Sodium ascorbate | 2,500 mg |
| D. | Pyridoxine hydrochloride | 1,000 mg |
| E. | Magnesium sulfate | 1,000 mg |
| F. | Adrenal cortex | 2,000 mcg |
| G. | Magnesium chloride | 2,000 mg |
| H. | Thiamine | 1,000 mg |
| I. | Heparin sodium | 5,000 U.S.P. units |
| J. | Calcium gluconate | 1,000 mg |
| K. | Calcium d-saccharate | 3.5 mg |

The above solution was intravenously infused to the patient in 500 ml units. Following treatment and reexamination, it was determined that the solution was effective in removing sclerotic plaques, with an attendant overall improvement in the state of the patient's health.

EXAMPLE II

Next, a series of controlled tests were conducted for the purpose of determining the minimum quantitative amounts of the constituents added to the standard Ringers injection which would still yield efficacious results in actual patient treatment. The results of these tests are summarized below and set forth these apparent minimum quantities. It is to be understood that a standard Ringers solution such as that set forth in the preceding Example I was also utilized in this Example II. It is also to be understood that the relative proportions of the constituents of the B-complex ingredient were maintained, and that the minimum quantity indicated relates to that total B-complex.

A. B-complex: 1,000 mg
B. Hydrochloric acid U.S.P.: 10 mg
C. Sodium ascorbate: 500 mg
D. Pyridoxine hydrochloride: 500 mg
E. Magnesium sulfate: 100 mg
F. Adrenal cortex: 250 mcg
G. Magnesium chloride: 250 mg
H. Thiamine: 100 mg
I. Herparin sodium: 2,500 U.S.P. units
J. Calcium gluconate: 250 mg
K. Calcium d-saccharate: 1.6 mg

EXAMPLE III

As in Example II, a series of tests were next conducted for the purpose of determining maximum desirable quantities of additives to the standard Ringers injection for preparing the solution of this invention. These results are summarized below in a fashion corresponding to that of Example II.

A. B-complex: 5,000 mg
B. Hydrochloric acid U.S.P.: 40 mg
C. Sodium ascorbate: 25,000 mg
D. Pyridoxine hydrochloride: 5,000 mg
E. Magnesium sulfate: 2,500 mg
F. Adrenal cortex: 2,500 mcg G. Magnesium chloride: 5,000 mg
H. Thiamine: 2,000 mg
I. Heparin sodium: 25,000 U.S.P. units
J. Calcium gluconate: 2,500 mg
K. Calcium d-saccharate: 5.0 mg As previously stated, treatment and observation of patients has further revealed that, dependent upon the individual patient's condition, medication in addition to the solution composition set forth in Examples I, II and III may be desirable. Accordingly, yet another series of experiments and tests were conducted for the purpose of identifying desirable additives, or "fortifiers," to be utilized in combination with the solution composition of this invention. The results of these tests are set forth in the ensuing Example IV.

EXAMPLE IV

Using the standard solution composition as set forth in the preceding Example I, a series of test were conducted whereby the following additional constituents were added to the basic solution for intravenous infusion in the quantities indicated. Attention is invited to the fact that the results tabulated below set forth not only the preferred quantities, but also observed maxima and minima. All quantities are set forth with regard to 500 ml of the solution of this invention. It is also to be understood that one, all, or any combination of the below constituents might be utilized during a single treatment.

| Constituent | Preferred | Maxima | Minima |
|---|---|---|---|
| Niacin | 500 mg | 1000 mg | 100 mg |
| $B_{12}$ | 500 mcg | 1000 mcg | 100 mcg |
| Ether | 5 cc | 10 cc | 2 cc |
| Algae | 500 mg | 1000 mg | 250 mg |
| Amino acids | 5 g | 10 g | 2 g |

It will thus be seen that the objects set forth above, among those made apparent from the preceding description, are efficiently attained, and since certain changes may be made in carrying out the above method and in the composition set forth without departing from the scope of the invention, it is intended that all matter contained in the above description shall be interpreted as illustrative and not in a limiting sense.

It is also to be understood that the following claims are intended to cover all of the generic and specific features of the invention herein described, and all statements of the scope of the invention which, as a matter of language, might be said to fall therebetween. Particularly, it is to be understood that in said claims, ingredients or compounds recited in the singular are intended to include compatible mixtures of such ingredients wherever the sense permits.

Now that the invention has been described, what is claimed is:

1. An intravenous solution for the treatment of arteriosclerosis, said solution consisting essentially of the following per 10 ml of standard Ringers injection:

a. B-complex: 1,000–5,000 mg
    b. Hydrochloric acid U.S.P.: 10–40 mg
    c. Sodium ascorbate: 500–25,000 mg
    d. Pyridoxine hydrochloride: 500–5,000 mg
    e. Magnesium sulfate: 100–2,500 mg
    f. Adrenal cortex: 250–2,500 mcg
    g. Magnesium chloride: 250–5,000 mg
    h. Thiamin: 100–2,000 mg
    i. Heparin sodium: 2,500–25,000 U.S.P. units
    j. Calcium gluconate: 250–2,500 mg
    k. Calcium d-saccharate: 1.6–5.0 mg.

2. An intravenous solution as in claim 1 further containing 100–1,000 mg niacin per 500 ml of said solution.

3. An intravenous solution as in claim 1 further containing 100–1,000 mcg $B_{12}$ per 500 ml of said solution.

4. An intravenous solution as in claim 1 further containing 2–10 cc ethyl ether per 500 ml of said solution.

5. An intravenous solution as in claim 1 wherein said B-complex is selected from the group consisting of methionine N.V., cholinechloride U.S.P., thiamine hydrochloride U.S.P., niacinamide U.S.P., riboflavin (as riboflavin-5'-phosphate sodium), pyridoxine hydrochloride U.S.P., and d'pantothenyl alcohol, all in benzyl alcohol N.F. 1.5% in water.

6. A method for treatment of arteriosclerosis comprising the intravenous infusing of the solution of claim 1 into a patient, in a therapeutically effective amount whereby plaques formed within the veins and arteries will be removed resulting in increased blood supply with an attendant increase in available oxygen and nutrients to body tissues.

7. An intravenous solution for the treatment of arteriosclerosis consisting essentially of the following per 10 ml of said solution wherein said solution has as its base standard Ringers injection:

a. Sodium Chloride: 86 mg
    b. Potassium chloride: 3 mg
    c. Calcium chloride: 3.3 mg
    d. B-complex: 2,185 mg
    e. Hydrochloric acid U.S.P.: 20 mg
    f. Sodium ascorbate: 2,500 mg
    g. Pyridoxine hydrochloride: 1,000 mg
    h. Magnesium sulfate: 1,000 mg
    i. Adrenal cortex: 2,000 mcg
    j. Magnesium chloride: 2,000 mg
    k. Thiamine: 1,000 mg
    l. Heparin sodium: 5,000 U.S.P. units
    m. Calcium gluconate: 1,000 mg
    n. Calcium d-saccharate: 3.5 mg.

8. An intravenous solution as in claim 7 further containing 500 mg niacin per 500 ml of said solution.

9. An intravenous solution as in claim 7 further containing 500 mcg $B_{12}$ per 500 ml of said solution.

10. An intravenous solution as in claim 7 further containing 5 cc ethyl ether per 500 ml of said solution.

11. An intravenous solution as in claim 7 wherein said B-complex consists essentially of:

a. Methioine N.V.: 125 mg
    b. Cholinechloride U.S.P.: 500 mg
    c. Thiamine hydrochloride U.S.P.: 500 mg
    d. Niacinamide U.S.P.: 1,000 mg
    e. Riboflavin (as riboflavin- 5'-phosphate sodium: 20 mg
    f. Pyridoxine hydrochloride U.S.P.: 20 mg
    g. d'Pantothenyl alcohol: 20 mg all in benzyl alcohol N.F. 1.5% in water.

* * * * *

UNITED STATES PATENT AND TRADEMARK OFFICE
CERTIFICATE OF CORRECTION

PATENT NO. : 4,167,562
DATED : September 14, 1979
INVENTOR(S) : H. Ray Evers, M.D.

It is certified that error appears in the above—identified patent and that said Letters Patent is hereby corrected as shown below:

Claim 6, line 22, "arterioslerosis" should read -- arteriosclerosis --.

Signed and Sealed this

Eighth Day of January 1980

[SEAL]

Attest:

SIDNEY A. DIAMOND

Attesting Officer   Commissioner of Patents and Trademarks